United States Patent [19]

Cini

[11] Patent Number: 5,387,517
[45] Date of Patent: Feb. 7, 1995

[54] THIOL ACTIVATED PROTEASE FROM STEM BROMELAIN FOR TREATING DEVITALIZED TISSUE

[75] Inventor: John K. Cini, Bethlehem, Pa.

[73] Assignee: Ethicon, Inc., Somerville, N.J.

[21] Appl. No.: 217,341

[22] Filed: Mar. 23, 1994

[51] Int. Cl.6 .................. C12N 9/48; D06M 16/00
[52] U.S. Cl. ................................. 435/212; 435/264
[58] Field of Search ............................. 435/212, 264

[56] References Cited

U.S. PATENT DOCUMENTS

| | | | |
|---|---|---|---|
| 2,977,287 | 3/1961 | Bloch et al. | 195/62 |
| 3,940,478 | 2/1976 | Kurtz et al. | 424/94 |
| 3,983,209 | 9/1976 | Schmitt | 424/78 |
| 4,122,158 | 10/1978 | Schmitt | 424/27 |
| 4,197,291 | 4/1980 | Klein et al. | 424/94 |
| 4,226,854 | 10/1980 | Klein et al. | 424/94 |
| 4,276,281 | 6/1981 | Crikelair | 424/84 |
| 4,286,064 | 8/1981 | Galbraith | 435/219 |
| 4,307,081 | 12/1981 | Klein et al. | 424/94 |
| 4,329,430 | 5/1982 | Klein et al. | 435/219 |
| 4,361,551 | 11/1982 | Galbraith | 424/94 |
| 4,613,502 | 9/1986 | Turkova et al. | 424/94 |
| 4,645,668 | 2/1987 | Pinnell | 424/94 |
| 4,732,758 | 3/1988 | Hurion et al. | 424/94 |
| 4,801,451 | 1/1989 | Hellgren et al. | 424/94.63 |
| 5,106,621 | 4/1992 | Rowan et al. | 424/94.65 |

OTHER PUBLICATIONS

Feinstein et al., (1964) *Biochemistry*, 3(8), 1050–1054, "On the Molecular Weights of the Proteolytic Enzymes of Stem Bromelain".

Ota et al., (1985) *J. Biochem.*, 98(1), 219–228, "Reinvestigation of Fractionation and Some Properties of the Proteotytically Active Components of Stem and Fruit Bromelains".

Vesterberg, O. et al., Isoelectric Fractionation, Analysis and Characterization of Ampholytes in Natural pH Gradients; Acta Chem. Scandinavica 20 (1966) pp. 820–834.

Rowan, A. D. et al., Ananain: A Novel Cysteine Proteinase Found in Pineapple Stem; Archives of Biochemistry and Biophysics., vol. 257, Nov. 15, 1988, pp. 262–270.

*Primary Examiner*—Douglas W. Robinson
*Assistant Examiner*—Jon P. Weber
*Attorney, Agent, or Firm*—Hal Brent Woodrow

[57] ABSTRACT

A purified thiol activated protease obtained from bromelain stem extract is provided. The protease has a molecular weight of about 17,000 daltons to about 21,000 daltons and an isoelectric point of about pI 4.5 to about pI 5.0. Methods for obtaining this enzyme and methods for use of this enzyme for debridement of eschar tissue are disclosed.

1 Claim, 5 Drawing Sheets

THIOL ACTIVATED PROTEASE FROM STEM BROMELAIN FOR TREATING DEVITALIZED TISSUE

FIELD OF THE INVENTION

This invention relates to a novel purified enzyme and a process for purifying this enzyme. This invention also relates to a method of treating devitalized tissue using this novel enzyme.

BACKGROUND OF THE INVENTION

Considerable efforts have been made to develop debridement preparations that are capable of distinguishing between viable and non-viable tissue. These debridement preparations make it possible to remove the devitalized tissue without surgery. Non-surgical debridement is desirable in virtually all disease processes where topically devitalized tissue needs to be removed from the viable organism such as decubitus ulcers, pressure necroses, incisional, traumatic, and pyogenic wounds, and ulcers secondary to peripheral vascular disease.

One area of debridement research that has attracted considerable attention is the use of proteolytic enzymes and other chemicals to effect the early debridement of eschar tissues resulting from burns. Devitalized burn tissue is an excellent culture medium for opportunistic infections in burn patients. Septicemia resulting from infections is the proximate cause of death for the majority of severely burned patients. Intensive investigations with chemical agents such as tannic acid, salicylic acid, and pyruvic acid as well as proteolytic enzymes such as papain, pinguinain, trypsin, and streptokinase have not led to satisfactory debridement. Chemical agents were found to cause further injury to already damaged tissue. Proteolytic enzymes were found to be too slow and to have toxic side effects or to attack viable tissue as well as devitalized tissue.

However, several enzyme preparation from bromelain-stem extract have been found to selectively remove eschar. Hydrated bromelain powder and crude extract were initially employed to remove eschar tissue with mixed results. Purified enzyme isolated from the bromelain stem extracts have proven to be effective in the debridement of eschar tissue. For example, Debridase (described in U.S. Pat. No. 4,329,430), Ananain and Comosain (described in EPA 313346A2) were all purified from bromelain stem extracts for use in debridement. With the extensive research that had been performed to isolate debridement enzymes from bromelain stem extracts it had been thought that all of the effective debridement enzymes in bromelain stem extracts had been already identified and isolated.

However, the present invention is directed to a novel debridement enzyme derived from bromelain stem extracts and methods for extracting and utilizing this enzyme to remove eschar tissue.

SUMMARY OF THE INVENTION

In accordance with the present invention, there is provided a purified enzyme preparation capable of debridement of devitalized tissue from a mammalian host comprising a thiol activated protease derived from bromelain stem extracts having an isoelectric point of in the range of from about pI 4.6 to about pI 5.0 and a predominate molecular weight in the range of from about 17,000 daltons to about 21,000 daltons.

In accordance with another embodiment of the present invention, there is provided a method of digesting devitalized mammalian tissue comprising contacting said tissue with a proteolytic enzyme preparation derived from bromelain stem having an isoelectric point of in the range of from about pI 4.6 to about pI 5.0 and a predominate molecular weight in the range of from about 17,000 daltons to about 21,000 daltons wherein said enzyme is provided in an amount effective to digest said devitalized tissue so that said devitalized tissue can be removed.

In accordance with yet another embodiment of the present invention, there is also provided a method for isolating a substantially purified enzyme preparation from a bromelain stem comprising removing materials with a molecular weight below 3000 from said bromelain stem extract thereby forming a clarified stem extract; then separating the novel debridement enzyme from the clarified stem extract by removing material with a molecular weight in the range of from about 17,000 to about 21,000 daltons and an isoelectric point in the range of from about pI 4.6 to about pI 5.0.

DETAILED DESCRIPTION

Figure 1:
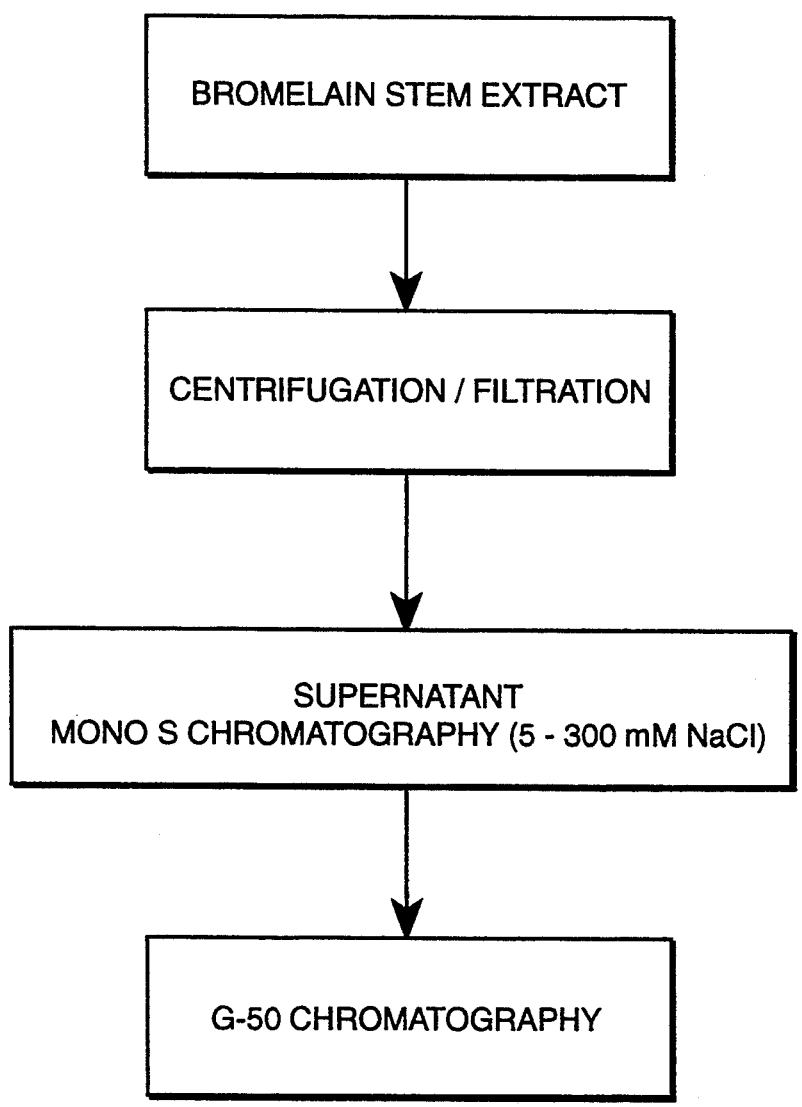
FIG. 1 provides a flow chart of one method for purifying the inventive debridement preparation ($\alpha$-Bromelain) from bromelain stem extract.
Figure 2:
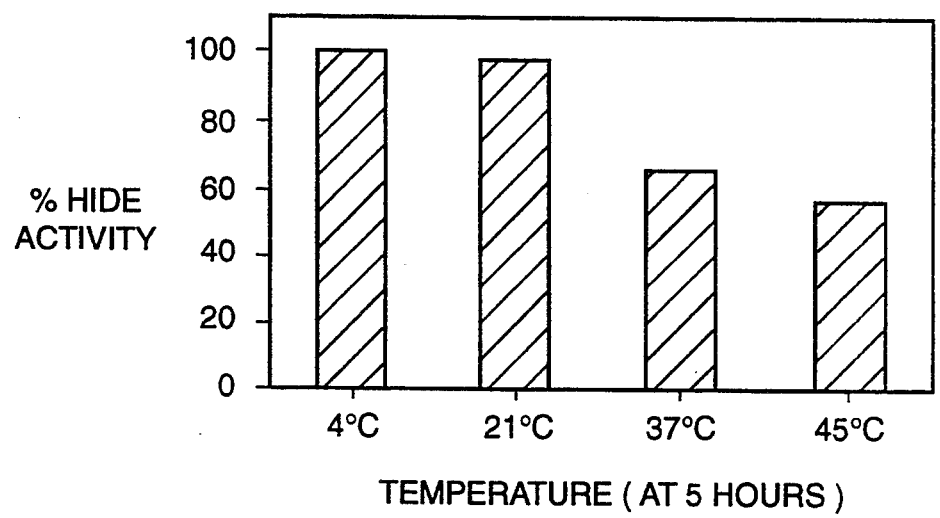
FIG. 2 provides a graphical illustration of temperature versus the inventive debridement preparation ($\alpha$-Bromelain) activity after 5 hours of incubation in the hide test described in Example 8.
Figure 3:
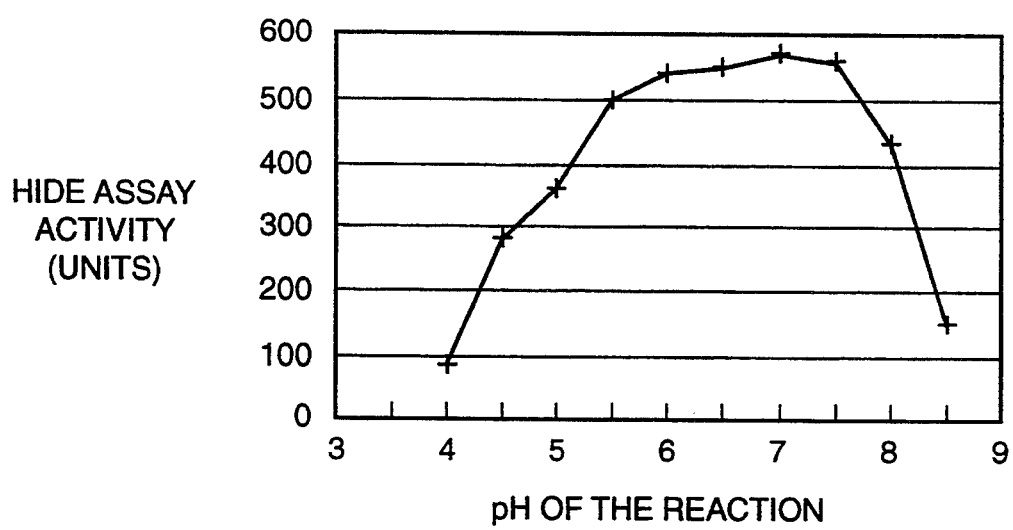
FIG. 3 provides a graphical illustration of pH versus the inventive debridement preparation activity ($\alpha$-Bromelain) in the hide test as described in Example 8.
Figure 4:
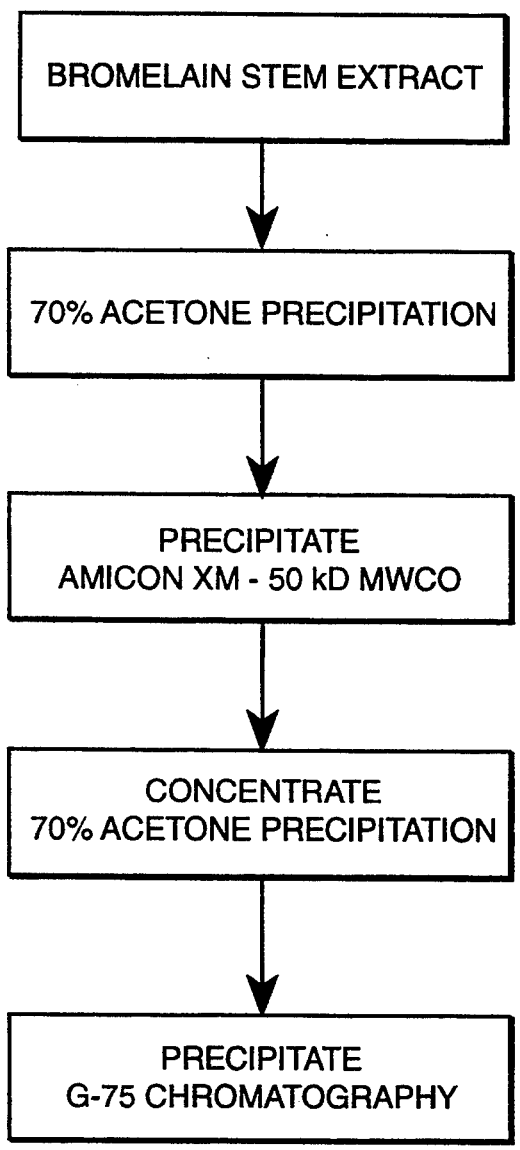
FIG. 4 provides a flow chart of one method for purifying Debridase.
Figure 5:
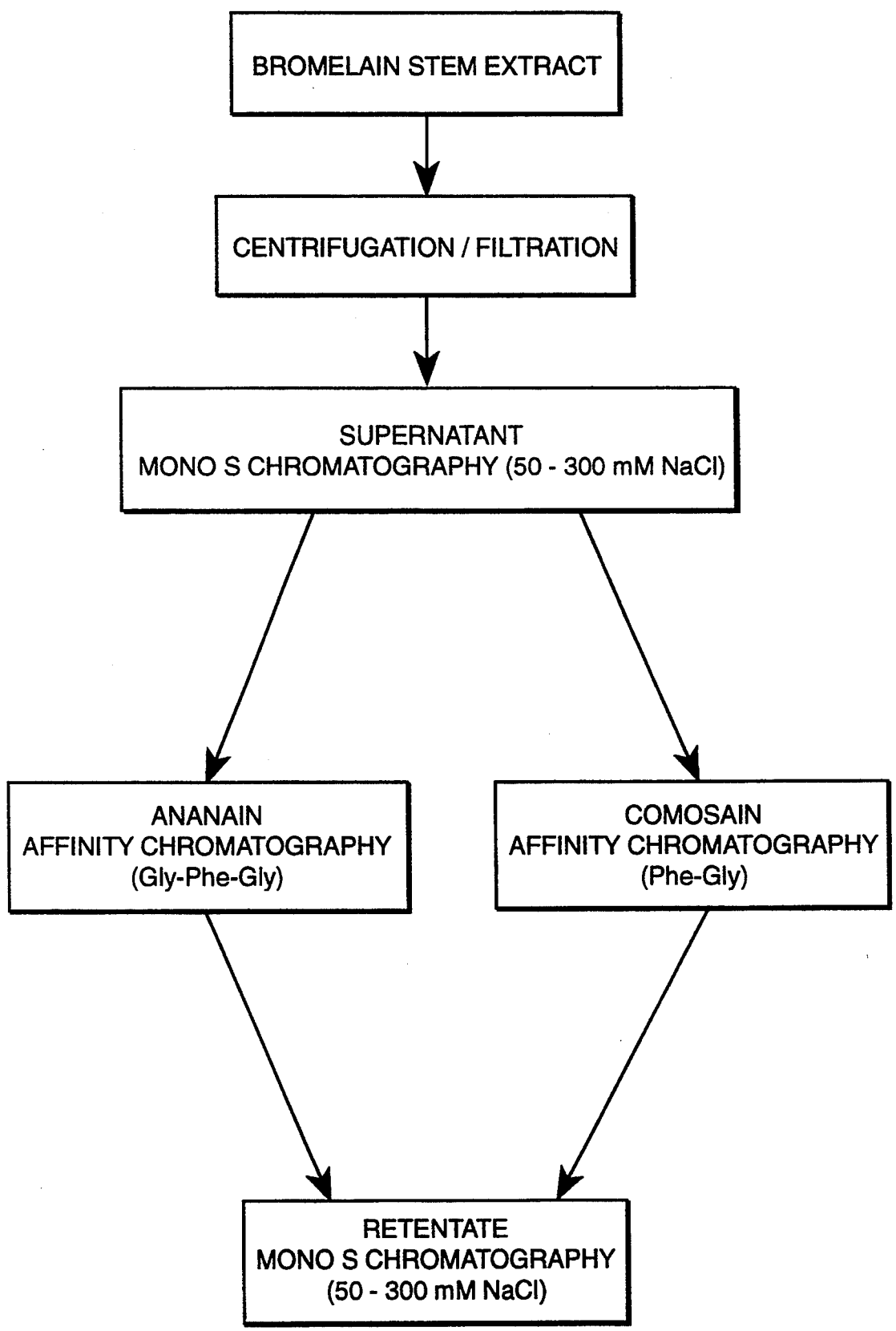
FIG. 5 provides a flow chart of one method for purifying Ananain and Comosain.

The present invention provides a novel proteolytic enzyme preparation useful for the therapeutic removal of devitalized tissue from mammals (i.e., domestic livestock and humans). The invention debridement preparation is hereinafter referred to as $\alpha$-Bromelain. $\alpha$-Bromelain is a proteolytic enzyme preparation isolated from bromelain stem. $\alpha$-Broemlain has an isoelectric point of in the range of from about pI 4.6 to about pI 5.0 and preferably is about pI 4.8. The molecular weight of $\alpha$-Bromelain is predominately in the range of 17,000 to 21,000 dalton and preferably is about 19,000 daltons.

The invention debridement preparation is heat labile and thiol activated.

The invention also includes physiologically acceptable alkali metal and acid addition salts of the α-Bromelain. The salts can be prepared by reaction in an aqueous medium between the α-Bromelain preparation and preferably a slight molar excess of the selected dilute alkaline metal base or acid, normally a mineral acid or a low molecular weight aliphatic carboxylic acid. Typically useful bases include sodium and potassium hydroxide. Acids which can be employed include hydrochloric and acetic acids.

α-Bromelain may be isolated from commercially available bromelain stem powder, which may be obtained from Sigma. α-Bromelain enzyme may be separated from the bromelain stem powder by a variety of techniques which utilize the unique characteristics of the novel α-Bromelain (such as the molecular weight and pI of the enzyme). For example the bromelain stem extract can be mixed into an aqueous solution then clarified by removing low molecular weight sugars and the like by precipitation (i.e. with cold 70% acetone). α-Bromelain may then be recovered form the clarified stem extract by separation processes which utilize the molecular weight difference of the inventive enzyme (such as difiltration or dialysis). This step may be proceeded or followed by a separation step based on the charge of the inventive enzyme (such as a cationic or anionic column separation). Those skilled in the art will recognize numerous other methods which may be used to recover α-Bromelain based on the inventive enzyme's physical characteristics.

Figure 6:
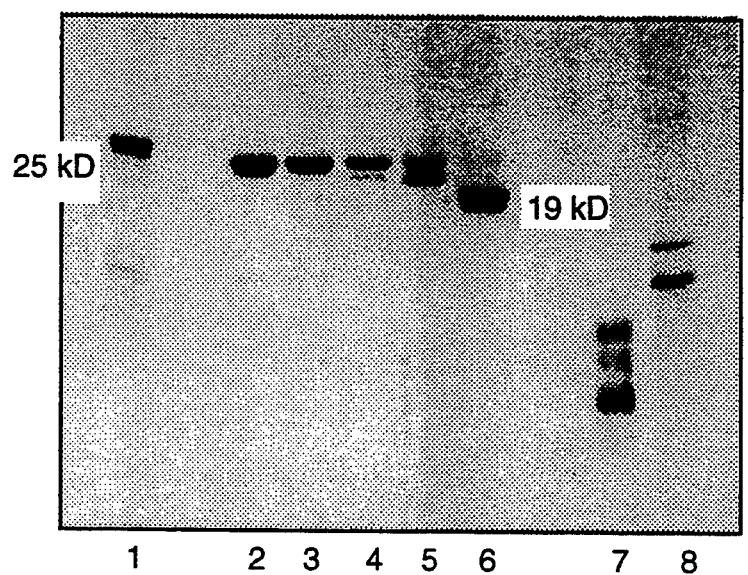
FIG. 6 graphically illustrates the results of a molecular weight comparison of crude bromelain extract (lane 1), Ananain and Comosain (lane 2), Bromelain II (lane 3), Bromelain I (lane 4), pooled Bromelain I and the inventive debridement preparation ($\alpha$-Bromelain) (lane 5), the inventive debridement preparation ($\alpha$-Bromelain) (lane 6) and molecular weight markers (lanes 7 and 8) by SDS-PAGE.

In the presently preferred procedure for isolating α-Bromelain, a crude extract of bromelain stem 10 grams is dissolved in 50 ml of 20 mM sodium acetate (pH 5.0), 0.1% mercaptoacetic acid (protease inhibitor) and mixed for 30 minutes at 4° C. The solution is centrifuged at 10,000×g for about 30 minutes to about 60 minutes at 4° C. The supernatant is then mixed to 70% cold acetone and centrifuged at 10,000×g for 30 minutes. The precipitate is dialyzed at 4° C. (3.5 kD bag) against 5 mM sodium acetate buffer (pH 5) and 0.1% mercaptoacetic acid the preparation is centrifuged and the supernatant saved. The supernatant was purified using a column containing Mono S (Pharmica) with sodium chloride concentration gradient from 5–300 mM NaCl the previously unidentified inventive thiol-activated protease appeared immediately after the break through peak. The supernatant from the Mono S column was pooled and lypholized. The lypholized supernatant was dissolved in buffer (2 ml of 20 mM sodium acetate, 0.1% mercaptoacetic acid at pH 5.5). The buffered solution was loaded on a 2×75 cm G-50 superfine (Pharmica) column equilibrated with the same buffer. The chromatographic conditions were a flow rate of 10–12 ml/min and fractions were collected in 3 ml tubes with the detection set at 280 nm. The column was standardized with molecular weights.

α-Bromelain is eluted at very low ionic strength, compared to Debridase, Bromelain I and II, Ananain and Comosain, which elute only at higher ionic strengths. A method for purifying the α-Bromelain is presented in FIG. 1. The purification process can be modified by those skilled in the art of protein purification to obtain α-Bromelain.

α-Bromelain prepared by the purification process in FIG. 1 is not a completely pure preparation. However, α-Bromelain is greater than 95% pure as demonstrated by SDS poylacrylamide gel electrophoresis in FIG. 6. A purification table for this purification process is presented in Example 1.

The physical characteristics of α-Bromelain were determined and compared to other known bromelain proteases. The molecular weight of the inventive debridement preparation and other known bromelain proteases were determined by SDS polyacrylamide gel electrophoresis (as described in Example 5). Electrophoresis of crude and bromelain extracts produced a composite of high and low molecular weight entities largely in the 25 kd range. See FIG. 6 lane 1. Ananain and Comosain (lane 2), and Bromelain II (lane 3) have major bands at 25 kd and minor bands at 22 kd and 16 kd. Bromelain I (lane 4) has a major band at 25 kd and a minor band at 22 kd. α-Bromelain (lane 6) has a major band at 19 kd and a diffuse band at 25 kd (less than 5%). These results indicate that α-Bromelain is a substantially pure enzyme with a different molecular weight than previously described in the literature for isolated bromelain proteases.

The isoelectric points of α-Bromelain, Ananain, Comosain, Bromelain I and Bromelain II were determined by an isoelectric focusing polyacrylamide gel electrophoresis (as described in Example 6). Ananain, Cosmosain, Bromelain I and Bromelain II all had isoelectric points of about 9.5 as reported in the literature. α-Bromelain had an isoelectric point in the range of from about pH 4.6 to about pH 5.0 and preferably was about 4.8. A g a i n , demonstration that α-Bromelain is a substantial different enzyme from the bromelain enzyme previously described in the literature.

Additionally, the amino acid composition of the α-Bromelain was also determined and compared to the amino acid composition of Ananain, Comosain, Bromelain I, Bromelain II, Papain, Actinidin, Cathepesin B and Pinguinain (as described in Example 7). The amino acid composition of α-Bromelain differs from the amino acid compositions reported for the other proteases.

In studies with hide and two synthetic fluorometric peptides (as described in Example 8), α-Bromelain demonstrated high specific activity in hydrolyzing hide and one of the two synthetic fluormetric peptides. α-Bromelain specific activity was inhibited by thioprotease inhibitors and partially inhibited by serine inhibitors and inhibited by Zn and Mg. The specific activity of α-Bromelain was also affected by pH and temperature. The optimal pH for α-Bromelain activity in the hide assay appears to be in the range of from about pH 5.2 to pH 8.2 and preferably will be employed at a pH in the range of from about 5.5 to about 7.5

The physical characteristics of α-Bromelain are markedly different from the other bromelain proteases conclusively demonstrating that the inventive debridement is a novel previously undescribed protease. The substrate specificity of the inventive debridement preparation also demonstrates a unique enzymatic activity profile when compared to other enzymes used for debridement.

The preparation obtained through the process described above may be immediately lyophilized to maintain its stability. Alternatively, the preparation may be filtered under sterile conditions to provide a sterile solution which may be packaged in an air tight vial or lyophilized to provide a sterile powder and stored at −20° C.

The lyophilized preparation may be prepared for application to devitalized tissue by dissolving or suspending the lyophilized powder in a suitable vehicle. Alternatively, concentrated solutions of the enzyme mixture can be further diluted with a vehicle, e.g., a viscous or semi-liquid vehicle (i.e., hydrogels).

A preferred composition for the administration of the is a sterile aqueous solution. Such solutions are readily prepared by dissolving up to 20% by weight of the lyophilized enzyme powder in water. When an aqueous solution is provided, it is preferred to prepare it immediately before use, since aqueous solutions have been found to slowly decompose. Just before application $\alpha$-Bromelain in a lyophilized powder can be dissolved in a 20 mM phosphate buffer pH 7.0 containing 10 uM DTT and placed in a pump spray.

Other methods useful for administration of $\alpha$-Bromelain of the invention include incorporating into aqueous solutions various gelling agents such as polyols, e.g., Carbopols, (available from Goodrich Chemical Co.) carboxyvinyl polymers e.g., Pluronics (available from BASF Corporation) Veegum HV (R. T. Vanderbilt Company, Norwalk, Conn.) and the like. These are buffered using various agents which provide a buffered pH of about 7.4 e.g., disodium phosphate ($Na_2HPO_4$) and imidazole. The buffering agents are generally used in concentrations of 0.05 to 0.2M. The gelling agents are generally used in concentrations of 1 to 2% for polyols and about 18% for carboxyvinyl polymers and about 6% for Veegum HV. Pluronic F-124 and Carabpols 940 and 934 and Veegum HV are presently preferred gelling agents. The formulations are prepared by mixing the vehicle, then adding the lyophilized enzyme mixture shortly (e.g., 1 hour) before use.

The formulations of $\alpha$-Bromelain may also be used with other active ingredients. For example, isolated purified sterile other enzymes (i.e., Travase, Debridase, Ananain and Comosain), antibiotics or other chemotherapeutic agents useful to prevent infection may be added to the formulations previously described.

For the purposes of treatment, $\alpha$-Bromelain should be applied to eschar tissue in an amount effective to remove devitalized tissue within 10 minutes to 24 hours, preferably within 1 to 8 hours. The amount of $\alpha$-Bromelain applied per square centimeter of eschar may vary depending on the amount of eschar tissue and condition of the treatment site. Generally, in the range of from about $1 \times 10^4$ to about $2 \times 10^6$ units of $\alpha$-Bromelain with a specific activity of about 20 in the hide test at 37° C. should be applied and preferably in the range of from about $1 \times 10^5$ to about $5 \times 10^5$.

The following non-limiting examples are provided to further illustrate the practice of the present invention.

EXAMPLE I 10 grams bromelain stem extract (Sigma) was dissolved in 50 ml of 20 mM sodium acetate (pH 5.0), 0.1% mercaptoacetic acid (protease inhibitor) and mixed for 30 minutes at 4° C. The solution was centrifuged at 10,000 $\times$ g for about 30 minutes at 4° C. The supernatant was then mixed to 70% cold acetone and centrifuged at 10,000 $\times$ g for 30 minutes. The precipitate was dialyzed at 4° C. (3.5 kD bag) against 5 mM sodium acetate buffer (pH 5) and 0.1% mercaptoacetic acid the preparation was centrifuged and the supernatant saved. The supernatant was purified using a column containing Mono S (Pharmica) with a sodium chloride concentration gradient from 5-300 mM NaCl the previously unidentified inventive thiol-activated protease appeared immediately after the break through peak. The supernatant from the Mono S was pooled and lypholized. The lypholized supernatant was dissolved in buffer (2 ml of 20 mM sodium acetate, 0.1% mercaptoacetic acid at pH 5.5). The buffered solution was loaded on a 2 $\times$ 75 cm G-50 superfine (Pharmica) column equilibrated with the same buffer. The chromatographic conditions were a flow rate of 10–12 ml/min and fractions were collected in 3 ml tubes with the detection set at 280 nm. The column was standardized with molecular weights. $\alpha$-Bromelain was collected following the void volume.

$\alpha$-Bromelain is eluted at very low ionic strength, compared to Bromelain I and II, Ananain and Comosain which elute at higher ionic strengths. The protocol for purifying $\alpha$-Bromelain is presented in FIG. 1. Table 1 below provides a purification table for the inventive enzyme.

TABLE 1

| PURIFICATION OF $\alpha$-BROMELAIN | | | | | |
|---|---|---|---|---|---|
| PROCEDURE | Total Units $\times 10^6$ | Total Protein mg | Specific Activity $\times 10^3$ | Yield % | Fold Purif. |
| Crude Prep | 4.5 | 309 | 11.5 | 100 | 1 |
| Mono 10/10 | 2.5 | 202 | 12.1 | 65 | 0.7 |
| G-50 | 0.38 | 120 | 19.2 | 39 | 2.4 |
| Final | 0.38 | 120 | 19.2 | 39 | 2.4 |

EXAMPLE 2

Purification of Debridase

A. Method for Debridase (Escharase) Purification

The method used was described in U.S. Pat. No. 4,329,430 by Dr. Klein with modifications.

All samples should have a minimal exposure to air as Escharase and other proteinase are easily oxidized and loss activity.

5 g of Bromelain powder (Sigma) was dissolved in 1 mM $PO_4$ + 0.1 mM $NaHS_2$ pH 4.0 21 ml mixed for 1 hour at 4° C. 9 ml of cold acetone was slowly added to the mixture to give a final concentration of 30% acetone. The two were mixed at 4° C. for 15 minutes. The liquid was then centrifuged at 3000 rpm (Beckman RT6000) for 15 minutes at 4° C.

30 ml of clear liquid supernatant was mixed with 40 ml of cold acetone to give a final concentration of 70% acetone, the 70 ml was mixed at 4° C. for 15 minutes. The liquid was then centrifuged at 3000 rpm (Beckman RT6000) for 15 minutes at 4° C. The precipitate was collected and mixed with 20 ml of 1 mM $PO_4$ pH 4.0 then Speed Vac to a powder at 25° C. overnight.

The powder (2.5 g) was dissolved in a 100 ml solution of 0.1M Na Acetate pH 5.5 and 1% mercaptoacetic acid and mixed at 4° C. for 30 minutes. The liquid was centrifuged at 3000 rpm (Beckman RT6000) for 15 min. at 4° C.

The solution was passed through an Amicon XM-50 filter under $N_2$ pressure (40 psi) while stirring at 4° C. for about 18 hours. A volume of about 5 ml concentrate and additional 30 ml of 0.1M sodium acetate, 1% mercaptoacetic acid was added and further concentrated to about 10 ml (this step was repeated three times). The concentrate (15 ml) was saved at $-20°$ C.

The filtrate was collected and concentrated (10 ml) over a Amicon YM-30 filter. A volume of 10 ml concentrate and additional 20 ml of a solution of 0.1M sodium acetate and 1% mercaptoacetic acid was added and further concentrate to about 20 ml (this step was repeated twice). The concentrate was resuspended in a 70% acetone solution. The solution was centrifuged at 3000 rpm (Beckman RT6000) for 15 minutes at 4° C.

The precipitate was mixed with 20 ml of a solution of 0.1M Na Acetate and 1% mercaptoacetic acid and lypholized overnight at 25° C. to a powder. The powder was weighed and 30 mg of the powder was dissolved in 2 ml of a solution of 20 mM sodium acetate and 1% mercaptoacetic acid (pH 5.5). The liquid was centrifuged at 2000 rpm (Beckman RT6000) for 15 minutes at 4° C.

3.0 ml of clear supernatant was loaded on a 2×75 cm G-75 column. The column was equilibrated with a buffer solution of 20 mM sodium acetate and 1% mercaptoacetic acid at pH 5.5.

Chromatographic conditions were as follows: flow rate was 10 ml/min and the fractions collected were 3 ml (60 drops about 150 tubes) with detection at 280 nm. Column was standardized with molecular weight markers blue dextran, 67 kD, 29 kD, 13 kD, 6.5 kD phenol red. Debridase has a MW about 40 kD.

The active Debridase was found at about 30 kD. Debridase was pooled and stored at −20° C. The sample was dialyzed in PBS buffer before using.

No specific in vitro assay exist for Debridase other than actual wound debridement. One general assay that was used was the hide assay described below.

Hide Assay

The assay buffer contains 0.4M phosphate, 8 mM DTT, 4 mM EDTA pH 6.8. Test samples (0.01 to 0.1 ml) ml were added to 0.2 ml of 0.01% Brij (to give a final volume 1 ml) then 0.1 ml of assay buffer was added and mixed and incubated for 5 minutes at 40° C.

Continuously mixed Hide (15 mg/ml) in 5% sucrose was added at 0.2 ml. The mixture was incubated for 20 minutes at 45° C. while shaking.

The reaction was stopped by adding 0.5 ml of 0.1M mono chloroacetate, 0.2M acetate, pH 4.3 (final volume of 1 ml). Mixture was centrifuged for 5 minutes at 2000 RPM. 0.2 ml of supernatant was read at 595 nm.

Standardization of activity was done by setting 100 units of activity equal to 50% substrate hydrolysis of Hide Substrate. This would be equal to 50% of the linear curve (of substrate utilization) measuring 595 nm.

A purification table based on the Hide assay of activity for the purification process described above is presented in Table 2 below.

TABLE 2
DEBRIDASE PURIFICATION TABLE

| PROCEDURE | TOTAL UNITS × $10^6$ | TOTAL PROTEIN mg | SPECIFIC ACTIVITY × $10^3$ | YIELD % | FOLD PURIFICATION |
|---|---|---|---|---|---|
| Crude | 26 | 6500 | 4.0 | 100 | 1.0 |
| 30% acetone | 23 | 7000 | 3.3 | 88 | 0.8 |
| 70% acetone | 20 | 6000 | 3.3 | 58 | 1.5 |
| X-50 concentrate | 3.5 | 400 | 8.8 | 14 | 2.2 |
| X-50 filtrate | 14.5 | 2400 | 6.0 | 56 | 1.5 |
| Y-30 concentrate | nd | nd | nd | nd | nd |
| 70% acetone | 4.2 | 250 | 16.8 | 16 | 4.2 |
| G-75 | 3.5 | 190 | 18.7 | 2.7 | 4.7 |

EXAMPLE 3

Method for the Purification of Ananain and Comosain

The method used to purify Ananain and Comosain was described in European Patent Application No. EP 0313462A2 by Drs. Rowan and Buttle of Strangeways Lab, with the following modifications.

All buffers were degassed and samples had a minimal exposure to air as cysteine proteinase are easily oxidized and loss activity.

Dissolve 10 g of Bromelain powder (Sigma) in a solution of 200 ml of 0.05M acetate, 1 mM EDTA and 0.01% azide at pH 5, was mixed for 30 minutes at 4° C. The mixture was then centrifuged for 30 minutes at a setting of 6000 RPM. The supernatant was passed through a 0.22 um Nalgene filter 250 ml with difficulty. The filtrate was kept at −20° C.

Chromatographic Purification

Mono S column 10/20 for Ananain and Comosain Purification

Stock buffer 1M Na,+1 mM EDTA,+40 g NaOH in 500 ml H$_2$O adjust to pH 5.5 with glacial acetic acid, and the solution was allowed to reach room temperature. 0.37 g EDTA was added and the pH as adjusted to pH 5.0. The final volume was filled to 2 L with H$_2$O, kept at 4° C.

Mono S HR 10/10 column was equilibrated first with 200 ml H$_2$O then with 1.0M Na+ in 200 ml of stock buffer. The column was then washed with 200 ml H$_2$O and finally with 200 ml of 0.05M Na+ stock buffer at a flow rate 0.5 ml/minutes.

3 ml of solution was applied to the Mono S column and 3 ml (60 drops/tube) fractions were collected into a tube containing 0.05 ml of a 0.1M hydroxyethyidisulphide (HED). The protein was eluted with a linear gradient from 0.05M of stock buffer to 2M over 240 minutes. Absorbance was measured at 280 nm. Tubes were sealed and stored at 4° C. for assay. Four peaks were detected; 1) unknown protease at 0.010 to 0.020M Na+; 2) Bromelain I at 0.30 to 0.35M Na+; 3) Bromelain II at 38 to 42M Na+; 4) Ananain and Comosain elute at 0.55 to 0.75M Na+.

The protein content was determined for peak #4. Peak #4 was concentrated and dialyzed on a Amicon YM-10 filter under N$_2$ against a solution of 0.05M phosphate:ethylene glycol (2:1), 1 mM EDTA, 0.01% azide, pH 6.8.

This peak was used for Ananain and/or Comosain purification.

Non-Specific Assay Method for Bromelain, Ananain and Comosain

Assay buffer contains 0.4M phosphate, 8 mM DTT, 4 mM EDTA pH 6.8. A test sample 0.01 to 0.1 ml of assay buffer was added to 0.2 ml of 0.01% Brij 35 (Brij volume was adjusted to give a final volume of 1 ml) and incubated for 5 minutes at 40° C.

Continuously mixed Hide (15 mg/ml) in 6% sucrose was added at 0.2 ml. The mixture was incubated for 20 minutes at 45° C. while mixing. The reaction was stopped by adding 0.5 ml of 0.1M mono chloracetate and 0.2M acetate at pH 4.3 (final volume 1 ml). The mixture was centrifuged for 5 minutes at 2000 rpm. 0.2 ml of supernatant was added to a 96 well plate and read on the $V_{max}$ reader at 595 nm.

Standardization of activity was done by setting 100 units of activity equal to 50% substrate hydrolysis of Hide. This would be equal to 50% of the linear curve (of substrate utilization) measuring 595 nm.

Affinity Chromatography for Ananain Purification 2.0 g of activated CH-Sepharose 4B (6 ml bed volume) was soaked overnight at 4° C. with 10 ml of 1 mM HCl and washed with 50 ml in the column 0.5×10 cm with 0.1M NaHCO$_3$, pH 8.0.

The 30 mg of GLY-PHE-GLY-SC was dissolved in 2.0 ml of methanol. 2.0 ml of 0.1M NaHCO$_3$ pH 8.0 was added and mixed in the column overnight at room temperature. The column was washed with 10 ml of a 10% methanol solution and then with 10 ml of H$_2$O. The column was then mixed with a 20 ml solution of 6% (v/v) aqueous ethanolamine (adjusted to pH 9.0 with HCl for 4 hours at 20° C., then washed with a solution of 10 ml H$_2$O and 0.1% azide and stored at 4° C.

Just before the affinity chromatograph step, the sample was aliquoted out into a 50 mg (21 ml) portions. 1.2 ml of a solution of 0.05M PO$_4$ (at pH 6.8) and DTT was added to each aliquot give a final concentration of 2 mM. The aliquots were left to activate for 20 minutes at room temperature. A 50 mg sample activated with DTT was loaded to the 6 ml affinity column (GLY-PHE-GLY-SC) with 4 ml of 0.05M PO$_4$ added and mixed for 1 hour at room temperature. This was followed by a 10 ml wash (saved for Comosain affinity) with a buffer solution of 0.05M phosphate:ethylene glycol (2:1), 1 mM EDTA and 0.01% azide at pH 6.8.

6 ml of a solution of 0.05M sodium formate: ethylene glycol (2:1), 1 mM EDTA and 0.01% azide at, pH 4.0 containing 0.05M HED was added to the column and left in the column overnight at 20° C. The column was then twice eluted with 6 ml (total 12 ml) of the same buffer as above and saved (Ananain) for the next Mono S column. The affinity column was washed with 20 ml a solution of 0.05M PO$_4$, pH 6.8, and 0.01% azide, then stored at 4° C.

Mono S column 10/10 for Ananain Purification

A Stock buffer of 29 g of NaCl+9.5 g of Na$_2$B$_4$O$_7$+0.37 g EDTA+0.1 g azide pH adjusted to 9.0 QS to 1 L was made.

Mono S HR 10/10 column was equilibrated first with 200 ml H$_2$O then with 100 ml (stock buffer) 0f 0.5M NaCl, 0.025M sodium tetraborate, 1 mM EDTA, 0.01% azide, pH 9.0. The column was then washed with 100 ml H$_2$O and finally with 0.02M NaCl buffer (stock buffer) flow rate 0.5 ml/minutes.

The column was eluted with a linear gradient of 0.01 to 0.3M NaCl in the stock buffer at a flow or 0.5 ml/minutes for 120 minutes. Fractions of 1 ml (20 drops) each were collected in tubes containing 0.01 ml of a 0.1M HED solution. The tubes were tested for activity against PHE-GLY-SC and Arg-Arg-Mec as described in the hide assay below. The tubes having activity against the PHE-GYL-SC (Ananain) or Arg-Arg-Mec (Comosain) were pooled and diluted with and equal volume of H$_2$O and 1 mM EDTA. The samples were dialyzed on a YM-10 filter (Amicon). The samples were concentrated down to 120 ml and diluted by to 50 ml of H$_2$O and 1 mM EDTA (this step was repeated 3 times). This step was then repeated with PBS 3 times. The final solution of Ananain or Comosain was reduced to 5 ml and stored at −20° C.

2.0 g of activated CH-Sepharose 4B (6 ml bed volume) was soaked overnight at 4° C. with 10 ml of 1 mM HCl and washed in the column 0.5×10 cm with 50 ml of a solution of 0.1M NaHCO$_3$, at pH 8.0.

The 30 mg of PHE-GLY-SC provided by BaChem Inc. was dissolved in 2.0 ml of methanol. 2.0 ml an aqueous of 0.1M NaHCO$_3$ solution at pH 8.0 was added and mixed in the column overnight at room temperature. The column was washed with 20 ml of a 10% methanol solution and then with 20 ml H$_2$O. The column was then mixed with 10 ml of a 6% (v/v) aqueous ethanolamine solution adjusted to pH 9.0 with HCl and stored for 4 hours at 20° C. The column was thereafter washed with 10 ml H$_2$O+0.01% azide and stored at 4° C.

Just before the affinity chromatography step, the sample was pooled with the samples, from the breakthrough and washed out step in the Ananain affinity chromatography. The sample was concentrated and dialyzed (YM-10 filter) against a solution of 0.05M PO$_4$ pH at 6.8. Then aliquoted out into two 2 ml portions. One 2 ml portion was added to a 1.2 ml aqueous solution of 0.05M PO$_4$ at pH 6.8 DTT was added to this sample to give a final concentration of 2 mM DTT. The sample was left to activate for 20 minutes at room temperature. The sample activated with DTT was loaded to the 6 ml affinity column (PHE-GLY-SC) with 4 ml of 0.05M P$_4$O added and mixed for one hour at room temperature. This was followed by a 10 ml wash (saved for use in Comasian affinity chromatography) with an aqueous buffer solution of 0.05M phosphate:ethylene glycol (2:1), 1 mM EDTA, 0.01% azide, pH 6.8.

6 ml of a solution of 0.05M sodium formate:ethylene glycol (2:1), 1 mM EDTA, 0.01% azide at pH 4.0 containing 0.05M HED was added to the column and left in the column overnight at 20° C. The column was then eluted twice with 6 ml (total 12 ml) of the same a buffer as above and saved (Comosain) for the next Mono S column. The affinity column was washed with 10 ml of a solution of 0.05M PO$_4$, pH 6.8, 0.01% azide and stored at 4° C.

Mono S column 10/10 for Comosain Purification

Stock buffer of 29 g of NaCl, 9.5 g of Na$_2$B$_4$O$_7$, 0.37 g EDTA, and 0.1 g azide with a pH adjusted to 9.0 Qs to 1 L was made.

The Mono S HR 10/10 previously described column was equilibrated first with 200 ml H$_2$O then with 100 ml of the stock buffer containing 0.5M NaCl, 0.025M sodium tetraborate, 1 mM EDTA and 0.01% azide at pH 9.0. The column was then washed with 100 ml H₂O and finally with a 5 percent solution of stock buffer having 0.01M NaCl buffer with flow rate 0.5 ml/minutes.

This column was eluted with a linear gradient of 0.02M NaCl to 0.3M of NaCl of the stock buffer at a flow of 0.5 ml/min for 120 minutes. Fractions of 1 ml (20 drops) each were collected in tubes containing 0.01 ml of a 0.1M HED solution. The tubes were tested for activity against Phe-Gly-MEC and Arg-Arg-Mec as described below. The tubes having activity specific for Phe-Gly-SC (Ananain) or Arg-Arg-Mec (Comosain) were pooled and diluted with and equal volume of H₂O and 1 mM EDTA. The sample was dialyzed on a YM-10 filter Amicon. The sample was dialyzed and diluted. The sample was concentrated down to 10 ml and diluted to 50 ml volume with an aqueous solution of 2 mM EDTA. The sample was then dialyzed and diluted with PBS three times. The final solution of Comosain or Ananian was reduced by to 5 ml and stored at −20° C.

The mono S HR 10/10 chromatogram and purification table are shown in Tables 3 and 4.

Specific Assay Methods for Ananain and Comosain

An activation buffer of 0.1M PO₄, 1 mM EDTA and 2 mM DTT at pH 6.8 was made for activity the enzyme samples.

The sample (0.01 to 0.1 ml) to be tested was added to 0.2 ml of 0.01% Brji 35 (Brij volume is adjusted to give a final volume 1 ml) then 0.1 ml of activation buffer was added and sample was incubated for 5 minutes at 40° C. 0.2 ml of 20 μm substrate in H₂O either Phe-Gly-MEC (specific for Ananain) or Arg-Arg-Mec (specific for Comosain) was added separately to different samples. The mixture was incubated for 15 minutes while mixing (final volume 1.0 ml). The reaction was stopped by adding 0.5 ml of 0.1M mono chloracetate and 0.1M acetate at pH 4.3. Activity was measured by an increase in fluorescence due to the release of Mec (ex. 360 nm, em. 460 nm). Standardization of activity was done by setting 100 units of activity equal to 50% substrate hydrolysis of Mec. This would be equal to 50% of the linear curve (of substrate utilization) measuring Fluor. Intensity.

Purification tables are provided for Ananain (Table 3) and Comosain (Table 4) below.

TABLE 3

PURIFICATION TABLE OF THE ANANAIN PREPARATION

| Procedure | Total Units × 10⁶ | Total Protein mg | Specific Activity × 10³ | Yield % | Fold Purific |
|---|---|---|---|---|---|
| Crude Prep | 49.5 | 4180 | 11.8 | 100 | 1 |
| Mono 10/10 | 7.9 | 950 | 8.3 | 16 | 0.7 |
| DiaVac | 0.8 | 96 | 8.7 | 1.6 | 0.7 |
| Affinity | 0.2 | 36 | 6/1 | 0.2 | 0.5 |
| Mono 10/10 | 0.16 | 40 | 4.1 | 0.16 | 0.4 |
| Final | 0.16 | 40 | 4.1 | 0.16 | 0.4 |

TABLE 4

PURIFICATION TABLE FOR THE COMOSAIN PREPARATION

| Procedure | Total Units × 10⁶ | Total Protein mg | Specific Activity × 10³ | Yield % | Fold Purific |
|---|---|---|---|---|---|
| Crude Prep | 49.5 | 4180 | 11.8 | 100 | 1 |
| Mono 10/10 | 7.9 | 950 | 8.3 | 16 | 0.7 |
| DiaVac | 0.8 | 96 | 8.7 | 1.6 | 0.7 |
| Affinity | 0.12 | 21 | 28 | 2.4 | 0.5 |
| Mono 10/10 | 0.38 | 10 | 19.2 | 0.8 | 2.4 |
| Final | 0.38 | 10 | 19.2 | 0.8 | 2.4 |

EXAMPLE 4

Purification of Bromelain I and II

Bromelain I and II were purified from bromelain stem powder (Sigma) following the procedure described by Rowan et al. in the *Archives of Biochemistry and Biophysics*, 1988, 267,262–270. As described by Rowan crude bromelain was dissolved in 25 mM sodium acetate/acetic acid buffer containing 1 mM EDTA, 0.01 percent sodium azide at pH 5.0. The solution was then clarified by passing through a 0.22 um filter. The clarified bromelain was then ran on an FPLC Mon S column as described by Buttle and Babrett in the *Journal of Biochemistry*, 1984, 223, 81–88 for the preparation of chymopapin, except the prior activation with dithiothreitol was omitted. The bromelain protein peaks I and II were collected separately and stored at −20° C.

EXAMPLE 5

Molecular Weight Comparison of Bromelain Stem Proteases

The molecular weights of the bromelain stem proteases were determined by SDS-PAGE. The SDS-PAGE was performed following the Laemmli Method described in *Nature*, 1991, 227, 680. Eight lanes of material were loaded on the SDS-PAGE. Lane 1 was loaded with crude aqueous bromelain extract. Lane 2 was a combination of Anaian and Comasain isolated as described in Example 3. Lanes 3 and 4 were Bromelain II and Bromelain I respectively, isolated as described in Example 4. Lane 5 contained the pooled Bromelain I and α-Bromelain. Lane 6 contained α-Bromelain. Lanes 7 and 8 contained molecular weights for comparison. The results of the SDS-PAGE are presented in FIG. 6.

The SDS-PAGE of the bromelain stem proteases demonstrates that α-Bromelain has a significantly different molecular weight compared to the bromelain proteases previously described in the art.

EXAMPLE 6

Isoelectric Point Comparison of Bromelain Stem Proteases

Figure 7:
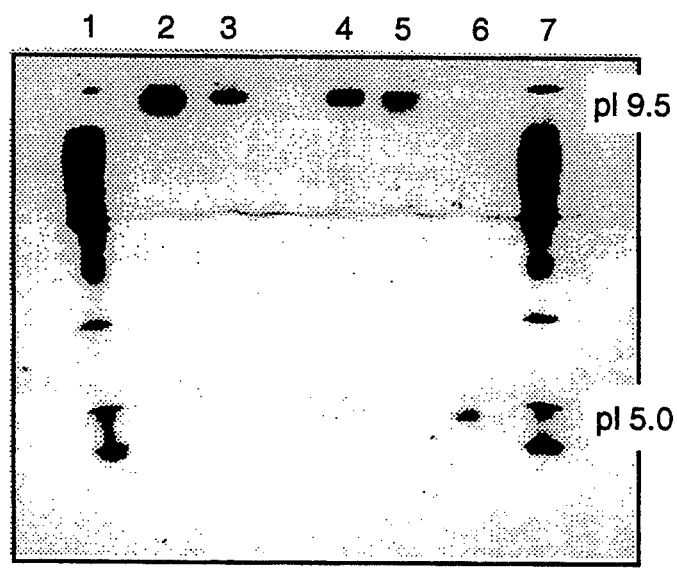
FIG. 7 graphically illustrates the results of an IEF-PAGE comparing Ananain and Comosain (lane 2), Bromelain II (lane 3), Bromelain I (lane 4), pooled Bromelain I and the inventive debridement enzyme ($\alpha$-Bromelain) (lane 5), the inventive debridement enzyme ($\alpha$-Bromelain) and pI markers (lanes 1 and 7).

The isoelectric point of the bromelain stem proteases were determined by IEF-PAGE using the LKB System number 1804-101 gel and a 2117 Multiphor II unit commercial available form (Pharmacia). Seven lanes of material were loaded on the IEF-PAGE. Lane 1 was loaded with pI markers. Lane 2 was loaded with a combination of Ananain and Comasain isolated as described in Example 3. Lanes 3 and 4 were loaded with Bromelain II and Bromelain I respectively, isolated as described in Example 4. Lane 5 was loaded with pooled Bromelain I and α-Bromelain. Lane 6 was loaded with α-Bromelain. Lanes 7 was loaded with additional pI markers. The results of the IEF-PAGE are presented in FIG. 7.

The IEF-PAGE of the bromelain stem proteases demonstrates that α-Bromelain has a significantly different pI compared to the bromelain proteases previously described in the art.

EXAMPLE 7

Amino Acid Comparison of Inventive Debridement Preparation of the Inventive Debridement Preparation and Other Proteases An amino acid comparison of α-Bromelain with Bromelain 1, Bromelain II, Comosain and Ananain was performed following the method described by Roth in the *Annals of Chemistry*, 1971, 43, 880-882. The result of this comparison were then compared to published sequences for Bromelain, Papain, Actinidin, Cathepsins B and Pinguinain. The results of this comparison are provided in Table 5 below. However, as indicated by the asterisks by the amino acid totals for α-Bromelain, Bromelain 1, Bromelain II, Comosain and Ananain, the totals do not include the content of cysteine and proline.

0.2 ml of continuously mixed Hide (15 mg/ml) in 6% sucrose was added to the sample. The mixture was incubated for 20 minutes at 45° C. while mixing.

The reaction was stopped by adding 0.5 ml of a solution of 0.1M mono chloroacetate, 0.2M acetate, pH 4.3 (final volume of 1 ml). The mixture was centrifuged for 5 minutes at 2000 rpm. 0.2 ml of supernatant was added to a 96 well plate and read at 595 nm.

Standardization of activity was done by setting 100 units of activity equal to 50% substrate hydrolysis of Hide. This would be equal to 50% of the linear curve (of substrate utilization) measuring 595 nm.

TABLE 6

ACTIVITY OF ENZYME PREPARATION USING SYNTHETIC AND NATURAL SUBSTRATES

| Preparation | Hide | Phe—Arg—Mec ** | Arg—Arg—Mec *** |
|---|---|---|---|
| | Units × 10$^4$/mg | | |
| Crude Bromelain Stem Extract | 50.0 | 50.0 | 550.0 |
| Debridase | 17.2 | 37.5 | 35.0 |
| Ananain | 0.58 | 7.4 | 2.0 |
| Comosain | 2.84 | 2.2 | 80.0 |
| α-Bromelain | 14.0 | 7.5 | 50.0 |
| | Units × 10$^4$/ml | | |
| Travase | 160 | 0.0 | 0.0 |

TABLE 5

| AMINO ACID | α-BROMELAIN | BROMELAIN I | BROMELAIN II | ANANAIN + COMPSAIN | BROMELAIN (a) | PAPAIN (b) | ACTINIDIN (c) | CATHEPSINS B (d) | PINGUINAIN (e) |
|---|---|---|---|---|---|---|---|---|---|
| Ala | 9 | 29 | 28 | 26 | 25 | 14 | 18 | 14 | 13 |
| Arg | 6 | 7 | 9 | 9 | 6 | 12 | 5 | 8 | 4 |
| Asx | 17 | 21 | 24 | 22 | 18 | 19 | 29 | 26 | 15 |
| Cyc | NA | NA | NA | NA | 7 | 7 | 7 | 14 | 5 |
| Gix | 16 | 18 | 18 | 19 | 16 | 20 | 20 | 23 | 10 |
| Gly | 38 | 29 | 27 | 29 | 22 | 28 | 28 | 33 | 19 |
| His | 2 | 1 | 2 | 2 | 1 | 3 | 1 | 8 | 2 |
| Ile | 7 | 18 | 17 | 19 | 17 | 12 | 17 | 16 | 11 |
| Leu | 14 | 11 | 10 | 11 | 6 | 11 | 8 | 9 | 8 |
| Lys | 9 | 16 | 16 | 15 | 15 | 11 | 8 | 9 | 9 |
| Met | 0 | 5 | 3 | 5 | 3 | 0 | 2 | 4 | 4 |
| Phe | 4 | 9 | 8 | 4 | 6 | 4 | 5 | 8 | 4 |
| Pro | NA | NA | NA | NA | 11 | 10 | 6 | 10 | 8 |
| Ser | 9 | 18 | 18 | 19 | 17 | 13 | 12 | 20 | 17 |
| Thr | 4 | 9 | 10 | 10 | 9 | 8 | 18 | 12 | 8 |
| Trp | 3 | 7 | 6 | 6 | 5 | 5 | 6 | 7 | 4 |
| Try | 6 | 14 | 15 | 15 | 14 | 18 | 14 | 12 | 14 |
| Val | 11 | 17 | 17 | 18 | 14 | 18 | 17 | 16 | 12 |
| TOTAL | 156* | 229* | 228* | 229* | 212 | 212 | 220 | 252 | 167 |

(a)As published in FEDS Lett.,1989, 247, 419.
(b)As published in Adv. Pro. Chem., 1971, 25, 79.
(c)As published in Biochore J., 1978, 173, 73.
(d)As published in Proc. Natl. Acad. Sci. U.S.A., 1983, 8, 3666.
(e)As published in Arh.Bloch., 1968, 126, 91.

*Hide 100 units = 0.1 ABS unit at 595 nm
**Phe—Arg 100 units = 0.2 Fluor. unit at Ex 360 / Em 460 nm
***Arg—Arg 100 units = 0.2 Fluor. unit at Ex 360 / Em 460 nm
+ Travase is a viscous gel. Enzyme activity extracted from 1 gram of gel.

EXAMPLE 8

In Vitro Activity Comparison of α-Bromelain to Other Proteases

Hide Method

The assay buffer contained 0.4M phosphate, 8 mM DTT, and 4 mM EDTA at pH 6.8.

A test sample (0.01 to 0.1 ml) ml was added to 0.2 ml of 0.01% Brij (to give a final volume 1 ml) then 0.1 ml of assay buffer was added and mixed. The sample was then incubated for 5 minutes at 40° C.

EXAMPLE 9

Inhibition Study of α-Bromelain and Other Bromelain Stem Proteases

Inhibition studies were performed on the bromelain proteases purified in Examples 1-4 to determine the effect of various enzyme inhibitor on these enzymes. All enzymes were set at 200 units activity/0.1 ml. The enzymes were preincubated with the inhibitors at 40° C. for 30 minutes, then assayed by the Hide method.

TABLE 7

| Inhibitor | Protease Class | Precent of Inhibition[1] | | | |
|---|---|---|---|---|---|
| | | α-Bromelain | Bromelain I | Bromelain II | Ananain + Comasin |
| E-64 50 uM | Thio-protease | 100 | 100 | 100 | 100 |
| PMSF 100 uM | Serine | 13 | 20 | 15 | 10 |
| DCIC 80 uM | Serine/ Elastase | 10 | 5 | 10 | 10 |
| Leupeptin 50 uM | Thio/ Serine | 100 | 100 | 100 | 100 |
| TPCK 60 uM | Serine/ Bromelain | 50 | 78 | 55 | 41 |
| TLCK 60 uM | Serine/ Bromelain | 81 | 80 | 70 | 90 |
| Antipain 50 uM | Plasmin | 100 | 100 | 100 | 100 |
| Bestatin 60 uM | Aminopeptidase | 0 | 0 | 0 | 0 |
| EDTA 10 Mm | Metallo-protease | 0 | 0 | 0 | 0 |
| Pepstatin 60 uM | Acid Protease | 10 | 15 | 10 | 5 |

[1]Hide Assay
[2]Inventive Debridement Preparation

Example 10

In Vitro Comparison of α-Bromelain to Other Proteases

In VIVO Evaluation

The in vivo evaluation was a blind study in three parts. In Study 1 Travase, Ananain, Comosain and Debridase were compared. In Study 2, the purified proteases; α-Bromelain, Bromelain I and II, and Ananian+Comosain were compared for their in vivo debridement activity.

All preparations were normalized for dosage by protein content (Study 1) or activity (Study 2). Post treatment evaluation was performed at 2 and 4 hours. All debriding agents were applied 24 hours post-burn on gauze pads into 1 cm×1 cm rubber dams. After 2 and 4 hours the pads are removed, the sites were scraped with a blunt scalpel to remove all loose eschar. The total wet weight of eschar removed at (2 and 4 hours) was determined and the eschar was dried to determine final dry weights.

The methods used for debridement were described by Dr. Ehrlich in *Burns*, 1990, 16, 243-246. A rat full-thickness burn injury model was used to evaluate debriding enzyme preparations. Full thickness scald burn injury was produced on each animal. Five male Sprague-Dawley rats, weighing 450 to 600 g, were anesthetized by an intraperitoneal injunction of Nembutal TM (50 mg/Kg, Abbott Laboratories, Illinois, USA, 50 mg/ml). The hair on the back was clipped and treated with Nair TM lotion (Carter-Wallace Inc., New York). The exposed skin, an area measuring approximately 7 cm×9 cm was immersed in a 100° C. waste bath for 15 seconds. This treatment has previously been shown to produce a full thickness scald burn injury. The animals were allowed to recover from the anesthetic and returned to their cages for 24 hours, during which period they were given food and water ad libitum. They continued to eat and drink and showed little, if any, discomfort.

Enzyme preparations were applied to wound eschar at 24 hours post-burn. Each animal was dosed with 0.5 ml of sample at two different times (2 hours apart). All samples determined as thiol-dependent proteases were activated with 0.6 ml of DTT buffer. All samples were kept on ice until applied. Treatment was performed on anesthetized rats using two rubber templates measuring approximately 3 cm×12 cm with three 1.5 cm×1.5 cm holes. The templates were placed symmetrically on the burn site. Accordingly, each burn site was divided into six treatment sites: 1) left upper; 2) left middle; 3) left lower; 4) right upper; 5) right middle; and 6) right lower. A thin layer of surgical gauze pads (approximately 1.5 cm×1.5 cm) was placed inside each square space and 1 ml of 10 mM sodium phosphate buffer (PBS) was added. The sites were maintained in this hydrated state by applying a Saran plastic wrap around each animal to cover all six sites simultaneously. The wrap was removed 20 minutes later and fresh gauze pads were placed in each site except in the upper left wound site, that site designated for treatment with Travase.

Two hours after initiation of enzyme treatment, the wound site gauze was carefully removed. Each treatment site was then scraped with a blunt spatula, with mild pressure, to remove all loose eschar, which was transferred to preweighted vials marked "2 hours". The extent of debridement was also scored visually at this time. New gauze pads were placed over the burn site and the enzyme samples reapplied. Wound eschar scrapings and visual scores were obtained at an additional 4 hours post-treatment interval. After wet weight determinations, the accumulated eschars were freeze dried and re-weighed to determine the final dry weight of the total debrided eschar. Eschar samples were lyophilized and dry tissue weights were used as a measure of the extent of the debridement process.

In Study 1, visual evaluation of debrided wounds indicates that Travase and the non-thiol Debridase are effective in eschar debridement (Table 8). Unfortunately, all weights of eschar obtained with Travase are grossly affected due to the oil/petrolatum base formulation. Therefore, weight comparisons cannot be performed with other test enzymes. Data from Studies 1 and 2 on the dry weights of removed eschar is presented in Tables 8 and 9.

TABLE 8

STUDY 1
DRY WEIGHTS OF REMOVED ESCHAR FOLLOWING DEBRIDING ENZYME TREATMENT
TOTAL DRY WEIGHT (mg) OF ESCHAR REMOVED (2 and 4 HOURS)

| Animal # | 1 | 2 | 3 | 4 | 5 | 6 | 7 | 8 | 9 | Average/SD |
|---|---|---|---|---|---|---|---|---|---|---|
| Travase* 2,000,000 units | 439 | 559 | 473 | 779 | 640 | 695 | 621 | 750 | 709 | 629 + 119 |
| Ananain** 8,000 units | 47 | 18 | 20 | 18 | 12 | 17 | 19 | 12 | 8 | 16 + 4 |
| Comosain** 30,000 units | 19 | 20 | 21 | 20 | 20 | 14 | 14 | 13 | 13 | 17 + 4 |
| Debridase** 180,000 units | 13 | 21 | 28 | 31 | 20 | 23 | 27 | 16 | 21 | 22 + 6 |
| Non-thiol-Debridase 180,000 units** | 13 | 16 | 12 | 16 | 19 | 23 | 16 | 15 | 15 | 15 + 4 |
| PBS*** | 12 | 21 | 13 | 23 | 21 | 11 | 36 | 55 | 10 | 22 + 14 |

*Travase contains 95% mineral oil and 5% polyethylene in a gel form accounting for the high weights. Activity is based on extraction method in UPS.
**1 mg of each protease was applied.
***10 mM sodium phosphate buffer solution

TABLE 9

STUDY #2
DRY WEIGHTS OF REMOVED ESCHAR USING PURIFIED ENZYMES

| Animal # PREPARATION | 1 | 2 | 3 | 4 | 5 | Average/SD |
|---|---|---|---|---|---|---|
| PBS* | 13 | 9 | 4 | 22 | 8 | 11 + 6 |
| Crude | 42 | 20 | 22 | 28 | 12 | 25 + 10 |
| α-Bromelain | 25 | 58 | 51 | 23 | 18 | 35 + 14 |
| Bromelain I | 41 | 25 | 45 | 29 | 24 | 33 + 8 |
| Bromelain II | 13 | 74 | 73 | 14 | 25 | 40 + 28 |
| Ananain + Comosain | 29 | 37 | 27 | 36 | 16 | 29 + 8 |

All enzymes were adjusted to 30,000 units of activity per application based on the Hide Assay
*10 mM sodium phosphate buffer

I claim:

1. A purified thiol activated protease obtained from bromelain stem extract capable of debridement of devitalized mammalian tissue, said protease having an isoelectric point of about pI 4.6 to about pI 5.0 and a molecular weight of about 17,000 daltons to about 21,000 daltons as determined by SDS-polyacrylamide gel electrophoresis.

* * * * *